United States Patent [19]

Smith et al.

[11] Patent Number: 5,690,622
[45] Date of Patent: Nov. 25, 1997

[54] OSTOMY BAG FILTERS

[75] Inventors: Rory James Maxwell Smith, Skipton; Paul Stephen Bird, Copthorne, both of United Kingdom

[73] Assignee: Welland Medical Limited, Crawley, United Kingdom

[21] Appl. No.: 765,603

[22] PCT Filed: Jun. 19, 1995

[86] PCT No.: PCT/GB95/01429

§ 371 Date: Dec. 31, 1996

§ 102(e) Date: Dec. 31, 1996

[87] PCT Pub. No.: WO96/01091

PCT Pub. Date: Jan. 18, 1996

[30] Foreign Application Priority Data

Jul. 1, 1994 [GB] United Kingdom ............... 9413227

[51] Int. Cl.$^6$ ............... A61F 5/44; A61M 1/00
[52] U.S. Cl. ............... 604/333; 604/327; 604/329; 604/355; 604/349; 128/DIG. 24
[58] Field of Search ............... 604/327, 329, 604/332, 333, 338, 342, 349, 355; 128/DIG. 24

[56] References Cited

U.S. PATENT DOCUMENTS

| | | | |
|---|---|---|---|
| 4,203,445 | 5/1980 | Jessup et al. | 128/283 |
| 4,230,761 | 10/1980 | Watts | 428/215 |
| 5,015,244 | 5/1991 | Cross | 604/344 |
| 5,108,382 | 4/1992 | Wright et al. | 604/342 |

FOREIGN PATENT DOCUMENTS

| | | |
|---|---|---|
| 0 226 439 | 6/1987 | European Pat. Off. . |
| 0 259 184 | 3/1988 | European Pat. Off. . |
| 0 273 611 | 7/1988 | European Pat. Off. . |
| 0 388 924 | 9/1990 | European Pat. Off. . |
| 0 475 608 | 3/1992 | European Pat. Off. . |
| 0 476 847 | 3/1992 | European Pat. Off. . |
| 2 385 598 | 10/1978 | France . |
| 2 638 634 | 5/1990 | France . |
| 1587604 | 4/1981 | United Kingdom ............... 604/344 |
| 2 083 762 | 6/1982 | United Kingdom . |
| 2 099 753 | 12/1982 | United Kingdom . |
| 2 211 196 | 6/1989 | United Kingdom . |
| 2 226 761 | 7/1990 | United Kingdom . |
| 2 273 052 | 6/1994 | United Kingdom . |
| WO 89/11262 | 11/1989 | WIPO . |
| WO 94/12128 | 6/1994 | WIPO . |

*Primary Examiner*—Robert A. Clarke
*Attorney, Agent, or Firm*—Lahive & Cockfield, LLP; Anthony A. Laurentano

[57] ABSTRACT

The invention provides a drainage bag for receiving bodily waste, the drainage bag comprises a water-impermeable inner bag (1) enclosed therein; means (6, 7) defining an orifice to enable bodily waste to be received by the inner bag (1); the outer (2) and inner (1) bags being detachably secured together in the region of the orifice (6, 7). A first opening (15) is provided in a wall (4a) of the water-impermeable inner bag, said first opening (15) being covered by a portion (16) of gas-permeable hydrophobic foam material; and a second opening (18) is provided in a wall of the water-impermeable outer bag (2), the second opening (15) being covered by a flatus filter (19); the disposition of the first (15) and second (18) openings being such as to allow flatus gases within the inner bag (1) to pass out through the first opening (15) and thence through the second opening (18) to atmosphere.

4 Claims, 4 Drawing Sheets

OSTOMY BAG FILTERS

BACKGROUND OF THE INVENTION

This invention relates to ostomy bag flatus filter arrangements and ostomy bags incorporating such arrangements. In particular, the invention relates to ostomy bags having a biodegradable inner bag and a waterproof disposable outer bag.

It is conventional to provide ostomy bags with filters to allow flatus gases to exit from the bag without producing unpleasant smells. Such filters typically take the form of a filter matrix formed from or incorporating an activated charcoal material, for example activated carbon cloth.

A problem with the filter assemblies known heretofore is that the contents of the bag can come into contact with the filter thereby either blocking the filter or gradually permeating into the filter itself.

Various attempts have been made to overcome this problem, but many such attempts have resulted in arrangements of somewhat complex construction which have complicated considerably the manufacture of the ostomy bag.

One known arrangement is disclosed in GB-A-2149306 and involves the provision of an interior barrier wall intended to shield the flatus filter from bodily waste as it enters the ostomy bag from the stomal orifice.

It is an object of the present invention to provide a flatus gas venting system for use with a two-bag ostomy bag arrangement which is simple and introduces minimal additional complexity to the manufacture of the bag.

SUMMARY OF THE INVENTION

Accordingly, in a first aspect, the invention provides a drainage bag for receiving bodily waste, the drainage bag comprising a water-impermeable outer bag; a water-impermeable inner bag enclosed therein; means defining an orifice to enable bodily waste to be received by the inner bag; the outer and inner bags being detachably secured together in the region of the orifice; characterised in that a first opening is provided in a wall of the water-impermeable inner bag, said first opening being covered by a portion of gas-permeable hydrophobic foam material; and a second opening is provided in a wall of the water-impermeable outer bag, the second opening being covered by a flatus filter; the disposition of the first and second openings being such as to allow flatus gases within the inner bag to pass out through the first opening and thence through the second opening to atmosphere.

With the exception of the second opening, the water-impermeable outer bag is otherwise gas-impermeable. As such, it may be formed from a material such as polyvinylchloride (PVC), polyvinyldichloride (PVDC), etheneyvinylalcohol and related materials and combinations thereof.

The inner bag may be formed of a material which is substantially gas-impermeable, or may be formed from a material which has a degree of gas-permeability.

The first opening is preferably located above the orifice through which bodily waste enters the bag.

The hydrophobic gas-permeable foam material can be, for example, a polyurethane foam material, such as the Kyroderm F grade available from Porvair Filtronics Ltd. of Shepperton, UK.

The porosity of the foam and the size of the aperture are preferably chosen so that flow rate of gas through the foam corresponds to the flow rate through the flatus filter in the outer bag wall.

The flatus filter covering the second opening, i.e. in the outer bag wall, is provided with means for deodorising flatus gases passing therethrough. Such deodorising means typically takes the form of an adsorbent carbon or charcoal material which may be in the form of carbon cloth, or in the form of activated charcoal distributed in a gas-permeable foam matrix.

Examples of such filters are disclosed in, for example, GB-A-2215605, GB-A-2202147, GB-A-2149306, and U.S. Pat. No. 4,203,445. Further examples of suitable flatus filters are provided in our earlier Application GB 9313194.4.

By means of the present invention there is provided a flatus gas venting system suitable for use in a two-bag ostomy bag arrangement which overcomes the aforementioned problems of flatus filters becoming blocked and/or waste materials becoming extruded through the filter, whilst not complicating the manufacture of the ostomy bags.

BRIEF DESCRIPTION OF THE DRAWINGS

The invention will now be illustrated by reference to one specific embodiment as shown in the accompanying drawings, of which.

DESCRIPTION OF ILLUSTRATED EMBODIMENT

Figure 1:
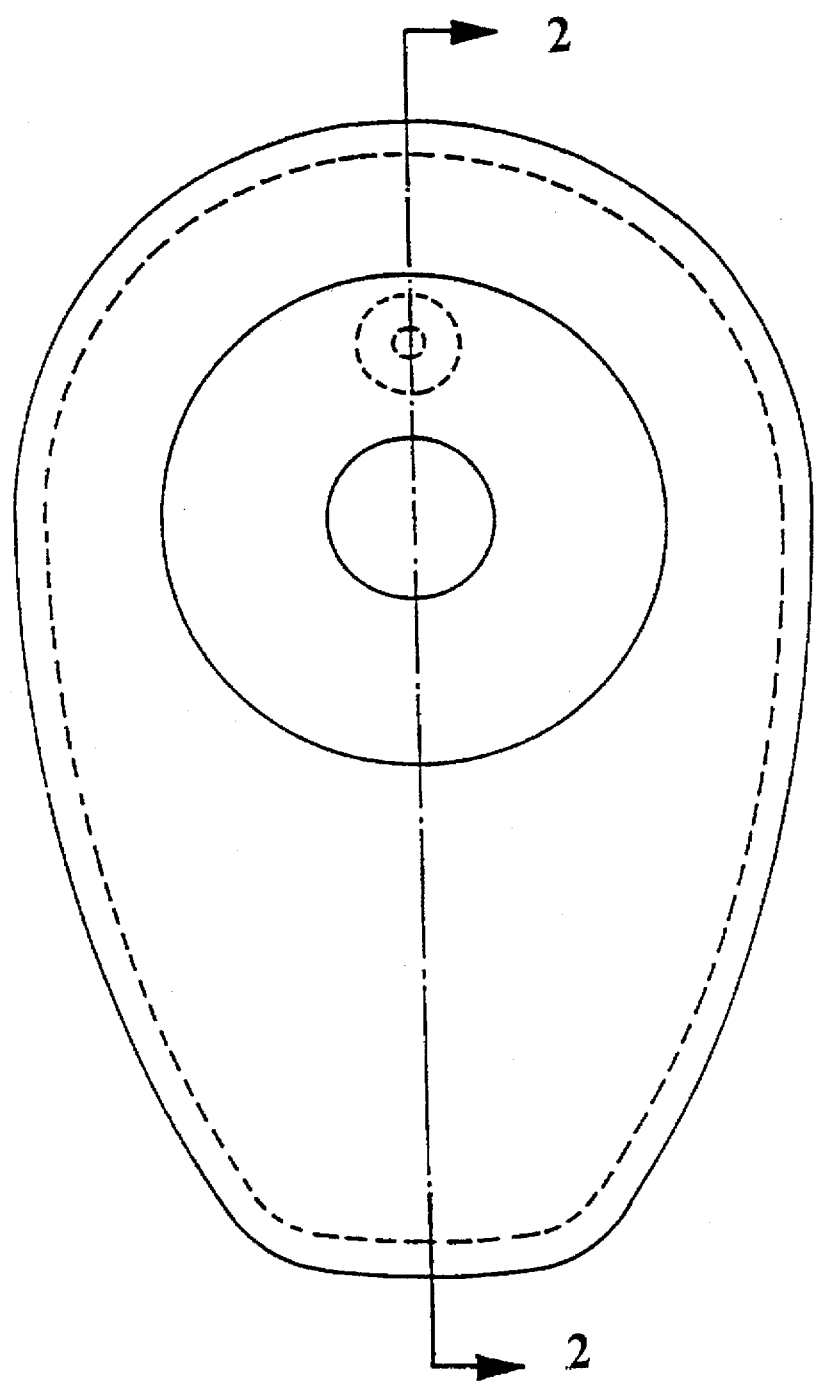
FIG. 1 is a plan view of an ostomy bag according to one embodiment of the invention.
Figure 2:
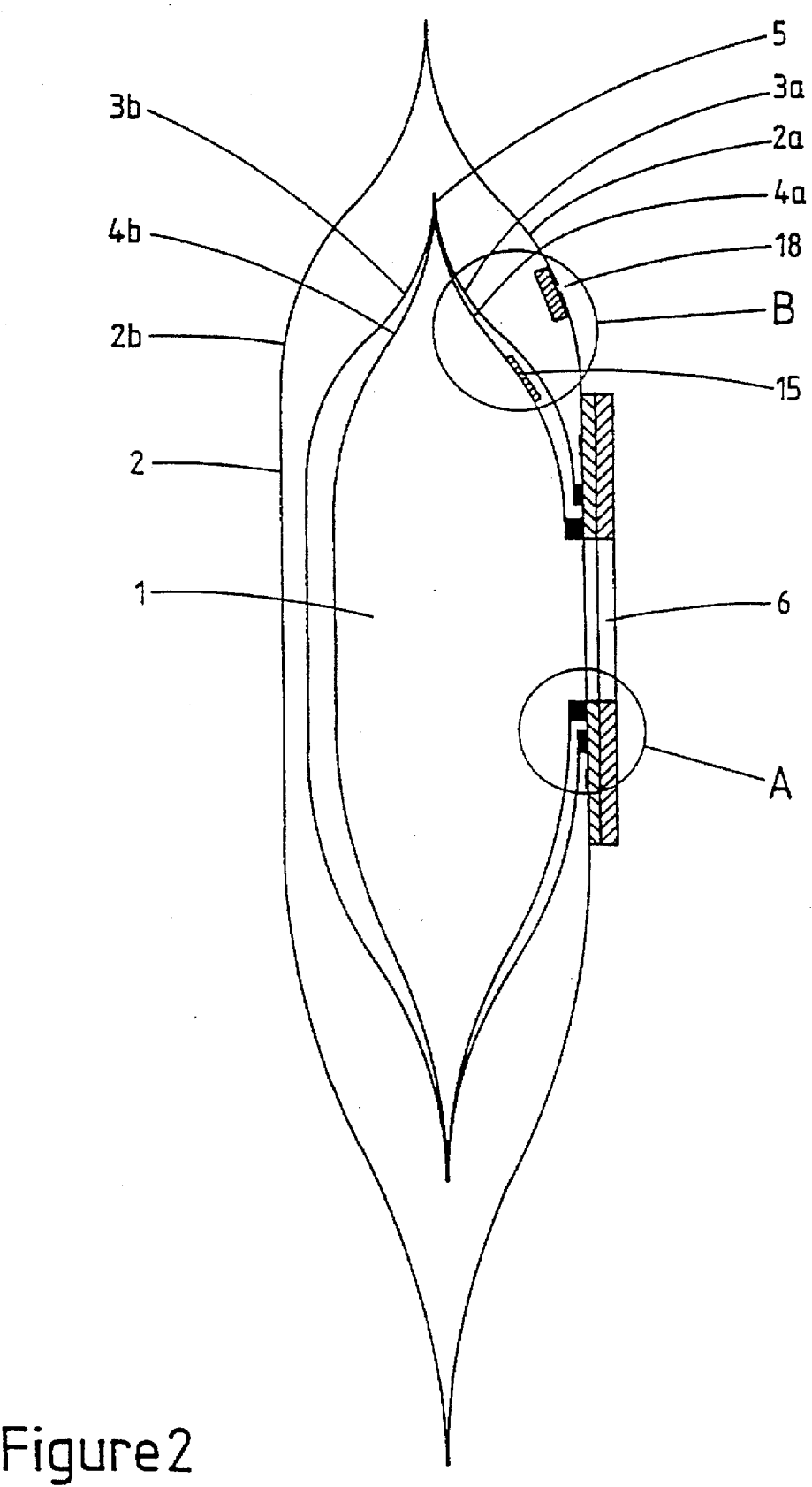
FIG. 2 is a sectional elevation along I—I of FIG. 1.

Referring now to the drawings, it can be seen that an ostomy bag in accordance with one embodiment of the present invention comprises an inner bag 1 and an outer bag 2 connected together via adhesive flange 7. Inner bag 1 comprises outer walls 3a, 3b and inner walls 4a, 4b defining an inner bag structure. Inner walls 4a, 4b are sealed together by heat welding at their peripheral margins 5, outer walls 3a, 3b being welded to the outer surfaces of the inner walls 4a, 4b respectively also at the peripheral margins 5.

The inner bag or liner 1 has an opening 6 through which the stoma (not shown) of a patient may protrude. The adhesive flange 7 surrounds the opening 6 and, in use, serves to secure the liner 1 to a body wall of the patient.

The inner wall 4a and outer wall 3a are each secured to the rear surface of adhesive flange 7, the inner wall 4a being secured to the flange at a position radially inwardly of the outer wall 3a.

The outer walls 3a, 3b are formed from a non-woven material comprising rayon fibres and PVA in the ratio 20:1. The rayon fibres are chosen such that the average length of the fibres is less than 8 mm, preferably less than 6 mm, and more preferably approximately 5 mm. The non-woven material is made by mixing the fibres together with the PVA and an appropriate amount of water, depositing the mixture on to a water-pervious moving conveyor, drawing water through the conveyor and transporting the resulting web through an oven to cure the mixture. The PVA serves to bind the rayon fibres together. However, once the non-woven material comes into contact with water, the PVA dissolves or disintegrates, thereby destroying the bonding between adjacent rayon fibres with the result that the non-woven fabric rapidly disintegrates.

The inner walls 4a, 4b in this embodiment are formed of a 30μ thick PVA film of a grade which is rapidly soluble in hot water, i.e. dissolves or disintegrates within 30 seconds at 50° C. in water, but at 38° C. is only very slowly soluble, and at room temperature is reasonably stable. An example of such a film is EC600 grade film available from NEDI of Middlewich, Cheshire, UK. Such film is not only soluble in hot water, but is also degraded by bacteria relatively quickly.

Figure 3:
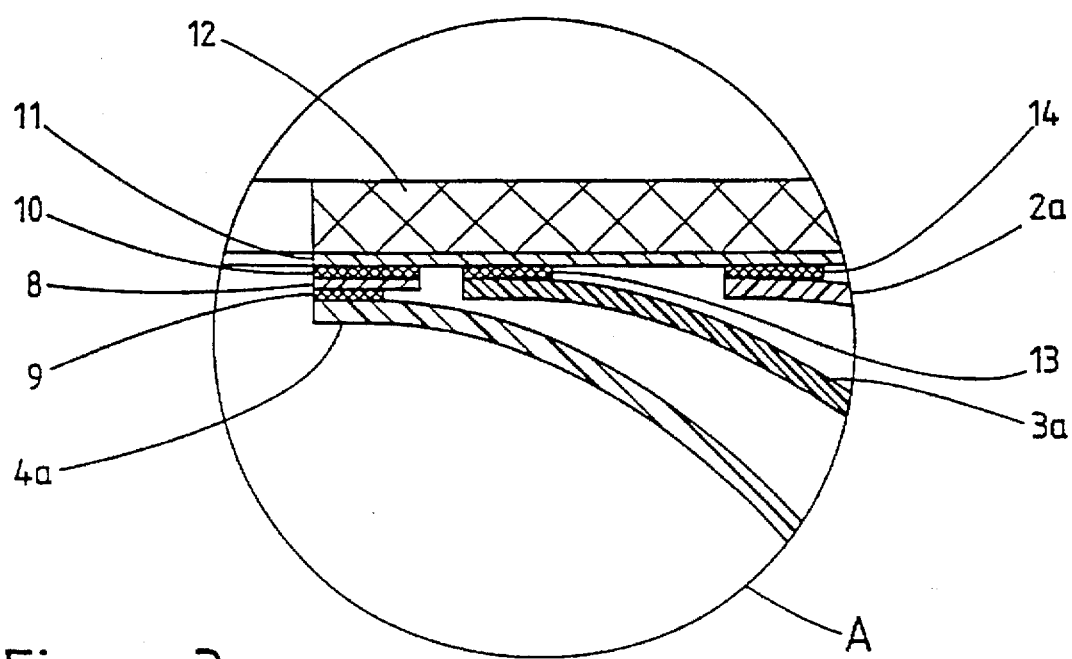
FIG. 3 is an enlarged sectional view of the region marked A in FIG. 2.
Figure 4:
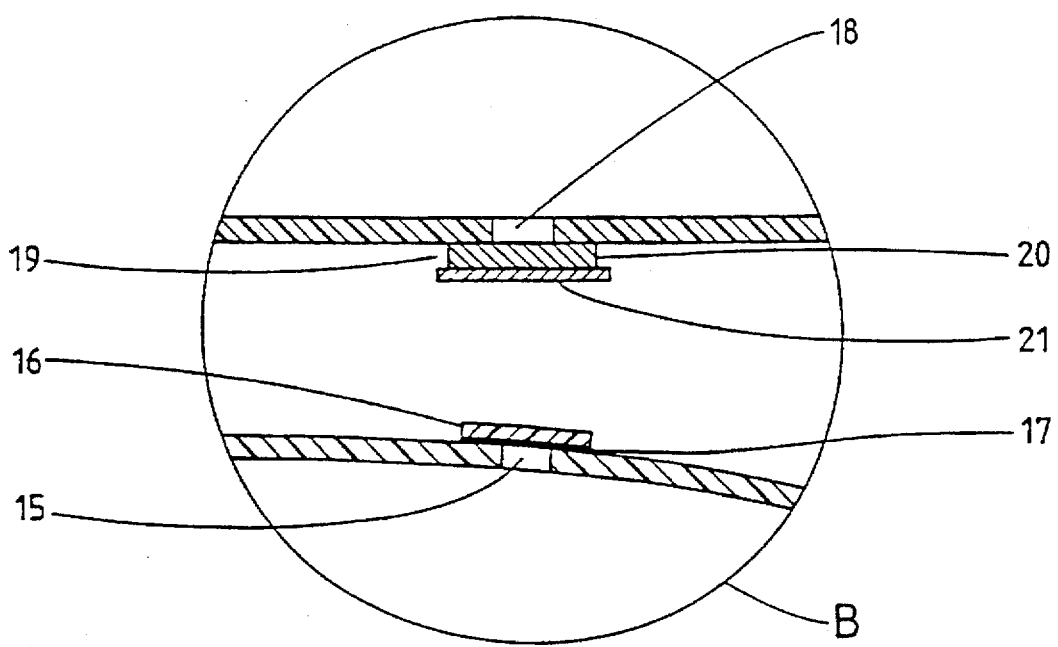
FIG. 4 is an enlarged of the section marked B in FIG. 2.

The manner in which the inner wall 4a is secured to the adhesive flange is shown in more detail in FIG. 3. From FIG. 3, it can be seen that the inner wall 4a is secured to an intermediate layer 8 of polyvinylchloride (PVC) film by means of intervening layer 9 of cyanoacrylate adhesive, and thence by adhesive layer 10 to PVC backing film 11 of the adhesive flange. Backing film 11 is coated with a thick layer of hydrocolloid adhesive 12 of known type.

The outer wall 3a of non-woven fabric, is secured to the PVC backing layer 11 of the adhesive flange by means of an adhesive layer 13 at a position radially outwardly of the joint with the inner wall 4a. The inner 4a and outer 3a walls are thus connected together, albeit indirectly, in the region of the adhesive flange as well as at the peripheral margins 5.

Enclosing the ostomy bag liner is an outer bag 2 formed from a water-impermeable gas-impermeable material such as polyvinylchloride (PVC), polyvinyldichloride (PVDC) or ethylenevinylalcohol polymer (EVA). Outer bag 2 is formed from two sheets 2a, 2b which are secured together by means of welding at their peripheral margins 2c. Outer bag 2 is secured to the rear surface of the adhesive flange 7 by means of annular peelable adhesive strip 14 which extends around the rear surface of the adhesive flange 7 at a position radially outwardly of the adhesive bond with the ostomy bag liner 1.

In accordance with the invention, the inner 1 and outer 2 bags are provided with a venting arrangement for allowing flatus gases to pass out into the atmosphere having first been deodorised.

Inner bag or liner 1 is provided with an opening 15 in the inner PVA wall 4a at a position above the level of the opening 6. By positioning opening 15 thus, the likelihood of bodily waste coming directly into contact with the opening is reduced. However, in order to prevent any bodily waste escaping through opening 15, whilst at the same time allowing flatus gases to pass therethrough, the opening 15 is covered by a disc 16 of a hydrophobic, gas-permeable polyurethane foam material; the disc 16 being secured to wall 4a by means of a layer of heat-fusible adhesive 17. The heat-fusible adhesive in this embodiment is applied in the form of PVA net or webbing and bonding is achieved by either a combination of heat and pressure, or RF welding.

The polyurethane foam is of a grade and porosity to enable flatus gases to be vented efficiently, and a suitable grade of foam is Kyroderm F.

Outer bag 2 is provided with an opening 18 which can be aligned with opening 15 in the inner wall 4a but need not be. Opening 18 is covered by a flatus filter 19 containing a deodorising agent such as activated charcoal. Filter 19 can comprise a layer 20 of activated carbon fabric, having a backing layer 21 of gas and water-impermeable material such as PVC, PVDC, EVA or polyester.

Figure 5:
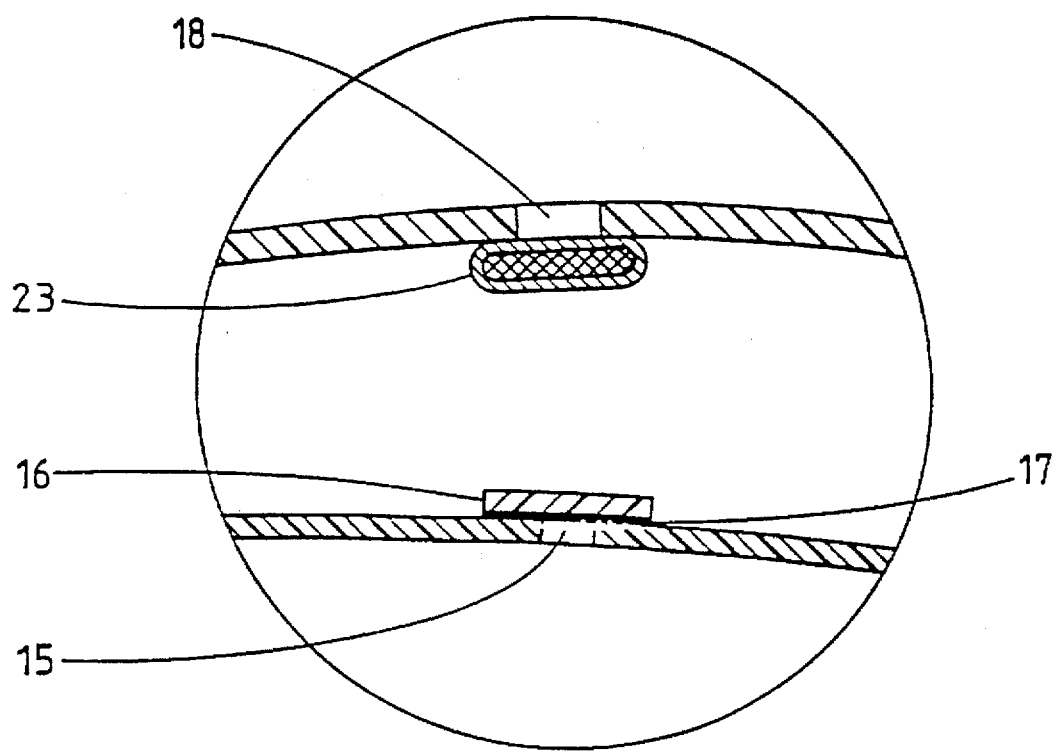
FIG. 5 is a fragmentary view corresponding to FIG. 4 but illustrating an alternative type of flatus filter.

Alternatively, a flatus filter 23 of the type illustrated in FIG. 5 may be used. Flatus filter 23 comprises a layer of carbon cloth 24 encapsulated with a surrounding layer 25 of a hydrophobic gas-permeable foam material, e.g. a polyurethane foam material. Examples of suitable materials and alternative forms of filter which can be used are disclosed in our earlier Application GB 9313194.4.

It will be appreciated from the foregoing that in use, flatus gases pass out through the hydrophobic foam disc 16 in the inner wall 4a, and through the outer wall 3a of non-woven material which is fully gas-permeable before entering the flatus filter 19 or 23 where odoriferous substances are removed by the activated carbon or charcoal before the gases pass out into the atmosphere.

The advantages of the venting system, in addition to its effectiveness in venting flatus gases whilst avoiding blockage by bodily waste materials, lie also in regard to its simplicity and ease construction.

It will readily be apparent that numerous modifications and alterations can be made to the specific embodiment illustrated in the drawings and described above, without departing from the principle underlying this invention. All such modifications and alterations are intended to be embraced by this Application.

We claim:

1. A drainage bag for receiving bodily waste, the drainage bag including a water-impermeable outer bag, a water-impermeable inner bag enclosed therein, means defining an orifice to enable bodily waste to be received by the inner bag, the outer and inner bags being detachably secured together in the region of the orifice, said bag comprising means defining a first opening in a wall of the water-impermeable inner bag, said first opening being covered by a portion of a gas-permeable hydrophobic foam material; and means defining a second opening in a wall of the water-impermeable outer bag, the second opening being covered by a flatus filter; wherein the disposition of the first and second openings allow flatus gases within the inner bag to pass through the first opening and hence through the second opening to atmosphere.

2. The drainage bag according to claim 1 wherein the hydrophobic gas-permeable foam material is a polyurethane foam material.

3. The drainage bag according to claim 1 wherein the portion of gas-permeable hydrophobic foam material is secured to the wall of the water-impermeable inner bag by means of a PVA fusible adhesive layer.

4. The drainage bag according to claim 1, wherein said first opening is located above the orifice through which bodily waste enters the bag.

* * * * *